(12) United States Patent
Von Arx et al.

(10) Patent No.: US 9,687,659 B2
(45) Date of Patent: Jun. 27, 2017

(54) CONDUCTIVE INTRA-BODY COMMUNICATION FOR IMPLANTABLE MEDICAL DEVICES

(71) Applicant: BIOTRONIK SE & CO. KG, Berlin (DE)

(72) Inventors: Jeffrey A. Von Arx, Lake Oswego, OR (US); Dirk Muessig, West Linn, OR (US); Hannes Kraetschmer, West Linn, OR (US); Habib Homayoun, Beaverton, OR (US); Larry Stotts, Tigard, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 164 days.

(21) Appl. No.: 14/290,761

(22) Filed: May 29, 2014

(65) Prior Publication Data

US 2014/0379048 A1    Dec. 25, 2014

Related U.S. Application Data

(60) Provisional application No. 61/838,890, filed on Jun. 25, 2013.

(51) Int. Cl.
*A61N 1/00* (2006.01)
*A61N 1/372* (2006.01)
(Continued)

(52) U.S. Cl.
CPC ......... *A61N 1/37276* (2013.01); *A61N 1/362* (2013.01); *A61N 1/37288* (2013.01);
(Continued)

(58) Field of Classification Search
USPC ...................................... 607/60, 30
See application file for complete search history.

(56) References Cited

U.S. PATENT DOCUMENTS 6,704,602 B2    3/2004   Berg et al.
2005/0197680 A1*  9/2005   DelMain ................ A61B 5/07
                                                                607/60
(Continued)

FOREIGN PATENT DOCUMENTS

WO    2013/082185 A2    6/2013

OTHER PUBLICATIONS

European Search Report received from EP Application Serial No. 14172892-1652, dated Nov. 28, 2014, 5 pages.

*Primary Examiner* — Nicole F Johnson
(74) *Attorney, Agent, or Firm* — ARC IP Law, PC; Joseph J. Mayo

(57) ABSTRACT

An implantable medical device including a data communication interface connected to a pulse generator. The pulse generator generates and delivers forward current pulses and reverse current pulses, wherein a polarity of the reverse current pulses is opposite to the polarity of the forward current pulses. Generates pulses representing binary digits, wherein a first kind of digits (1 or 0) is represented by a current pulse, and a second kind of digit respective of the other type of binary digits (0 or 1) is represented by a pause between current pulses. The data communication interface together with the pulse generator deliver current pulses with strictly alternating polarity such that every other current pulse is a reverse current pulse of opposite polarity compared to an immediately preceding forward current pulse. Thus, every string of current pulse is both, charge balancing and information encoding.

18 Claims, 5 Drawing Sheets

(51) Int. Cl.
*A61N 1/362* (2006.01)
*A61N 1/39* (2006.01)
*A61N 1/05* (2006.01)

(52) U.S. Cl.
CPC ............ *A61N 1/057* (2013.01); *A61N 1/0565* (2013.01); *A61N 1/3727* (2013.01); *A61N 1/37223* (2013.01); *A61N 1/39* (2013.01)

(56) References Cited

U.S. PATENT DOCUMENTS

| | | | |
|---|---|---|---|
| 2010/0030012 A1* | 2/2010 | Meskens | A61N 1/36032 600/25 |
| 2010/0249867 A1* | 9/2010 | Wanasek | A61B 5/0428 607/28 |
| 2010/0274218 A1* | 10/2010 | Yodfat | A61M 5/1413 604/504 |
| 2012/0109236 A1 | 5/2012 | Jacobson et al. | |

* cited by examiner

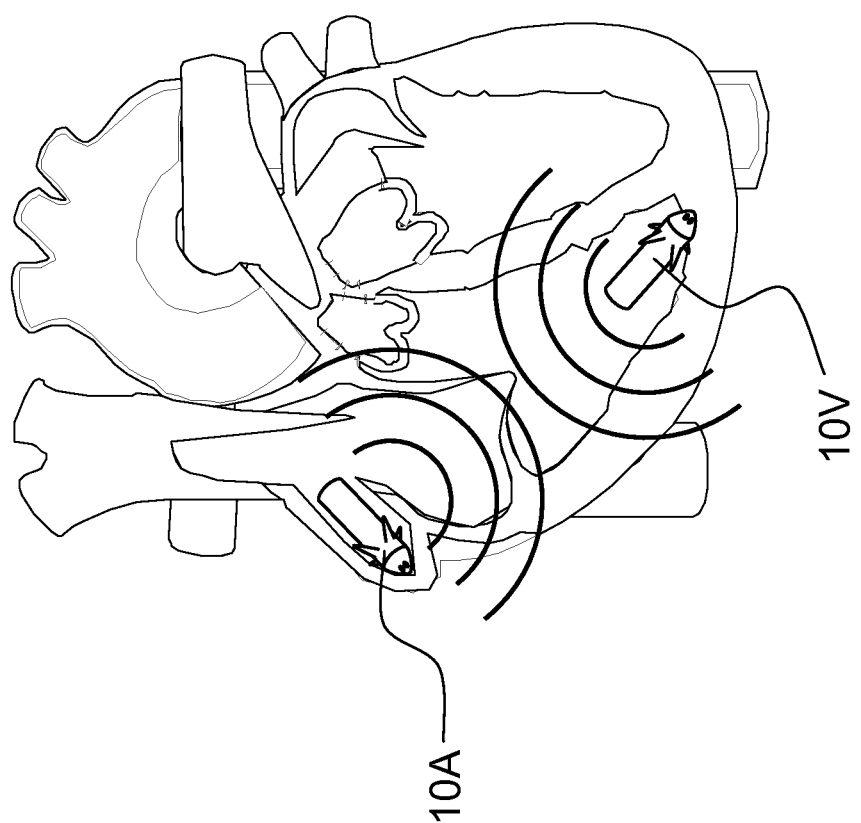

CONDUCTIVE INTRA-BODY COMMUNICATION FOR IMPLANTABLE MEDICAL DEVICES

This application claims the benefit of U.S. Provisional Patent Application 61/838,890, filed on 25 Jun. 2013, the specification of which is hereby incorporated herein by reference.

BACKGROUND OF THE INVENTION

Field of the Invention

Embodiments of the invention generally relate to implantable medical devices that communicate using intra-body conductive communication and a method for data communication via electric conductive body tissue.

Description of the Related Art

Conductive communications for implantable medical devices are disclosed inter alia from U.S. Pat. No. 6,704,602 to Berg et al., entitled "Implanted Medical Device/External Medical Instrument Communication Utilizing Surface Electrodes", and United States Patent Publication 2012/0109236 to Jacobson et al., issued as U.S. Pat. No. 9,168,383, entitled "Leadless Cardiac Pacemaker with Conducted Communication".

The implantable medical devices of Berg et al. and Jacobson et al., teach the use of current pulses to represent a logical "1", and teach that a lack of a current pulse is used to represent a logical "0", for conductive data communication.

BRIEF SUMMARY OF THE INVENTION

It is an object of at least one embodiment of the invention to provide an improved medical device. It is a further object to provide an improved method for communication via electric conductive body tissue.

At least one embodiment of the invention includes an implantable medical device having a data communication interface and a pulse generator. The data communication interface, in one or more embodiments, is operatively connected to the pulse generator. In at least one embodiment, the pulse generator may be configured to generate and deliver forward current pulses and reverse current pulses, wherein a polarity of the reverse current pulses is opposite to the polarity of the forward current pulses. According to one or more embodiments, the generator may be controlled by the data communication interface, and the data communication interface together with the pulse generator may generate pulses representing binary digits, wherein a first kind of digits (1 or 0) is represented by a current pulse, and a second kind of digits respective of the other type of binary digits (0 or 1) is represented by a pause between current pulses. The data communication interface together with the pulse generator, in at least one embodiment, may deliver current pulses with strictly alternating polarity such that every other current pulse is a reverse current pulse of opposite polarity compared to an immediately preceding forward current pulse. Thus, in one or more embodiments, every current pulse may be both, charge balancing and information encoding.

By way of at least one embodiment of the invention, the implantable medical device may apply a bipolar encoding scheme known as alternate mark inversion or modified alternate mark inversion, where a binary "0" is encoded as zero volts as in unipolar encoding, and a binary "1" is encoded alternately as a positive voltage and a negative voltage.

One or more embodiments of the invention include a method for data communication via electric conductive body tissue. In at least one embodiment, current pulses are used to represent binary digits. According to one or more embodiments, the method may include one or more of:

providing one or more time slots, wherein each time slot is provided for one binary digit;

delivering, in a respective time slot of said one or more time slots, a forward or a reverse current pulse if a logical "1" is to be transmitted in the respective time slot, or delivering no current pulse if a logical "0" is to be transmitted in the respective time slot; and, alternating a polarity of the current pulses such that a next logical "1", or "0", is represented by a current pulse of opposite polarity than a respective anteceding current pulse.

By applying this kind of coding scheme in a medical implantable device, a number of benefits are achieved simultaneously: At least one advantage being that a need for additional charge balancing pulses is avoided, since every other current pulse representing a logical "1" or "0" is balancing the immediately preceding current pulse. Thus, in one or more embodiments, the power requirements for data communication (transmission of data strings) are approximately cut in half compared to data transmission schemes used in known medical devices, since both, forward current and reverse charge balancing current pulses, are used to communicate information. According to one or more embodiments, since charge balancing is performed on implantable device electrodes to ensure there is no corrosion, using the charge balancing current to convey information is an innovative way to cut the current draw of conductive communication into roughly half. For example, in a typical implantable medical device, the charge balancing current happens a fixed time after stimulation. However, by way of at least one embodiment of the invention, delaying the charge balancing current until the next logical "1" time slot in conductive communications ensures that charge balancing occurs while utilizing the charge stored in the electrode/tissue interface to power the transmission of that binary digit (bit).

Thus, the device according to at least one embodiment of the invention and the method according to at least one embodiment of the invention require less battery capacity to achieve the same result as known implantable devices. Technically, this results in either a smaller-volume implant or in an implant with longer longevity.

In one or more embodiments of the invention, the first kind of binary digits is a logical "1" which is represented by a current pulse, and the second kind of binary digits is a logical "0" that is represented by an absence of a current pulse. The current pulses, in at least one embodiment, each representing a logical "1", are of strictly alternating polarity. Thus, the advantages pointed out above are achieved. Alternatively, in one or more embodiments, a logical "0" may be represented by a current pulse, and a logical "1" may be represented by an absence of a current pulse, thus generating a modified alternate mark inversion code.

According to at least one embodiment, the data communication interface together with the pulse generator may be configured to provide time slots, wherein each time slot represents one binary digit. In at least one embodiment, the time slots are all of a same duration.

By way of one or more embodiments, in order to avoid longer periods with no current pulse or with continuous current pulses (either representing a logical "0" or a logical "1", depending on which coding scheme is applied), the implantable medical device, and in particular the data communication interface, may perform a whitening transformation of a data string prior to transmission. In at least one embodiment of the invention, avoiding longer periods of no current pulse, and long periods of continuous current pulses has three advantages: First of all, this ensures that charge balancing occurs in time. Second, clock synchronization of a transmitting and a receiving device is facilitated. Third, the peak current demands from a battery are eased since long consecutive transmit current string are avoided. In one or more embodiments, a bit balanced encoding schema such as 8B/10B encoding (see U.S. Pat. No. 4,486,739) may be used, rather than data whitening, to avoid a long string of consecutive "1"s or "0"s.

According to one or more embodiments, the pulse generator includes pulse delivery circuitry, including a capacitor through which a forward current pulse is delivered so that the capacitor is charged upon delivery of a forward current pulse. In at least one embodiment, the pulse delivery circuitry may further include at least one switch that allows discharging of the capacitor in order to generate a reverse current pulse. Therefore, in at least one embodiment, the capacitor thus effectively causes charge balancing and data transmission using a single action.

According to at least one embodiment of the invention, the pulse generator is configured to deliver forward current pulses and backward current pulses, which each include the same amount of charge, or nearly the same amount of charge, to ensure charge neutrality on the electrodes. In one or more embodiments, the electrodes may include surface electrodes of the implantable medical device or electrodes connected to the implantable medical device.

The implantable medical device in at least one embodiment may be further configured to generate and deliver sub-threshold current pulses for data communications. The current pulses, in at least one embodiment, may include sub-threshold current pulses having low amplitude, narrow pulse width, and high frequency, or some combination of these. Thus, unintended tissue stimulation is avoided.

In one or more embodiments of the invention, the implantable medical device may be a stimulation device that may deliver both, sub-threshold current pulses for data communications and supra-threshold current pulses for stimulation. In at least one embodiment, the medical implantable device may be a cardiac pacemaker, an implantable cardioverter/defibrillator (ICD) or the like.

According to one or more embodiments of the method, prior to transmission of data strings, the whitening transformation of the data strings to be transmitted may be performed.

In at least one embodiment, the time slots provided may each have a same duration to facilitate clock synchronization.

The current pulses delivered, according to at least one embodiment, may each include essentially the same amount of charge in order to achieve charge neutrality over time.

According to at least one embodiment of the invention, each forward current pulse may be delivered via a capacitor, such that the capacitor is charged upon delivery of a respective forward current pulse, and the capacitor is discharged upon delivery of a reverse current pulse.

In one or more embodiments, the forward current pulses and the reverse current pulses may be sub-threshold current pulses having an intensity below a capture threshold of body tissue in order to avoid unintended tissue stimulation.

In at least one embodiment of the invention, every other current pulse may be a reverse current pulse, in order to achieve a sequence of current pulses of strictly alternating polarity.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 5 illustrates intra-body communication between two implantable leadless pacemakers that together act as two chamber pacemaker.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
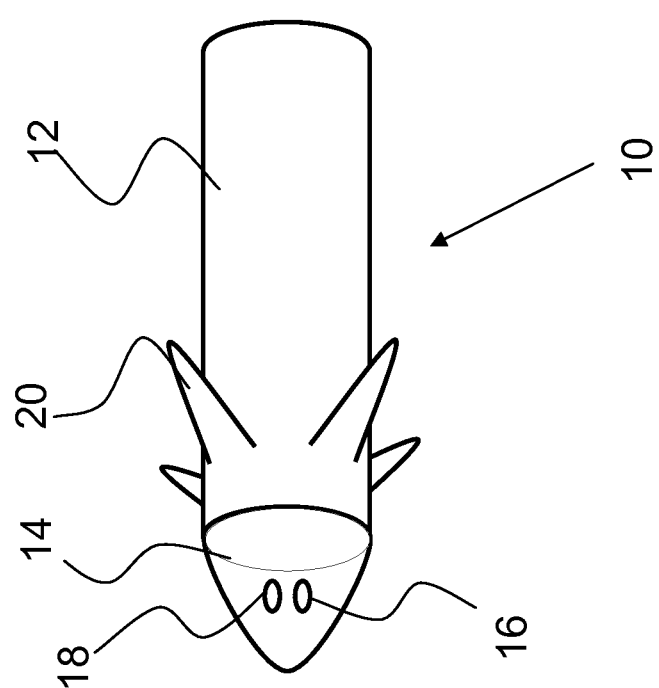
FIG. 1 is a schematic representation of an implantable leadless pacemaker (iLP).

FIG. 1 illustrates an implantable leadless pacemaker 10 that is implemented as an implantable medical (stimulation) device. In at least one embodiment of the invention, pacemaker 10 exhibits an elongated cylindrical case 12 with a hemispherical cap 14. Close to the apex of cap 14, in one or more embodiments, two small surface sensing and stimulation electrodes 16 and 18, may be provided. Alternatively, in at least one embodiment, electrode 16 may be located at a distal end of the pacemaker 10 and electrode 18 may be located at a proximal end of the pacemaker 10. In one or more embodiments, hooks or tines 20 may be included to allow anchoring of the pacemaker 10 in a heart chamber.

According to at least one embodiment, case 12 may be tightly attached to cap 14 in order form a hermetically closed housing. Electrodes 16 and 18, in at least one embodiment, may be integrated in cap 14 and may exhibit an electrically conducting surface that is electrically isolated with respect to the housing. In one or more embodiments, case 12 may be formed as a hermetically closed housing with isolated electrodes 16 and 18 at distal and proximal end of the case respectively. In at least one embodiment, electrodes 16 and 18 are surface electrodes that serve as poles for stimulation of heart tissue. Electrodes 16 and 18, in at least one embodiment, may be used as electrodes for conductive intra-body communications. The housing of pacemaker 10, in one or more embodiments, such as case 12, may act as a large surface electrode for conductive intra-body communication.

Figure 2:
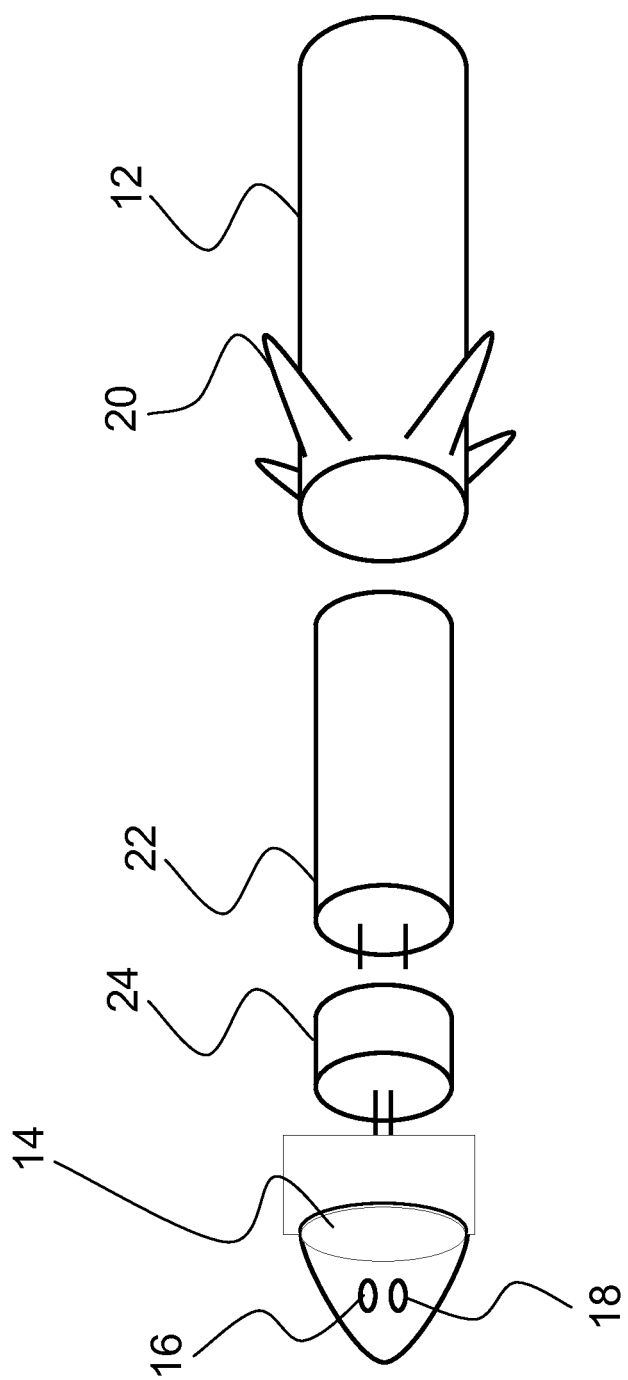
FIG. 2 is a schematic exploded view of the pacemaker in FIG. 1.

In FIG. 2, an exploded view of the pacemaker of FIG. 1 is illustrated to show components that are enclosed by pacemaker can or case 12. In at least one embodiment of the invention, the components may include one or more of a battery 22 and an electronics module 24. The electronics module 24, in one or more embodiments, may include one or more of a pacemaker control electronics device and a stimulation pulse generator. In one or more embodiments, the pacemaker may be a demand pacemaker, and may further include sensing units that pick up and process electric potentials from heart tissue.

According to at least one embodiment of the invention, the pacemaker may include a small battery 22 (~0.5 cm$^3$) with a minute capacity (~200 mAh). In one or more embodiments, the pacemaker uses conductive communication techniques for telemetry, in order to minimize the impact on the battery and battery capacity consumption.

Figure 3:
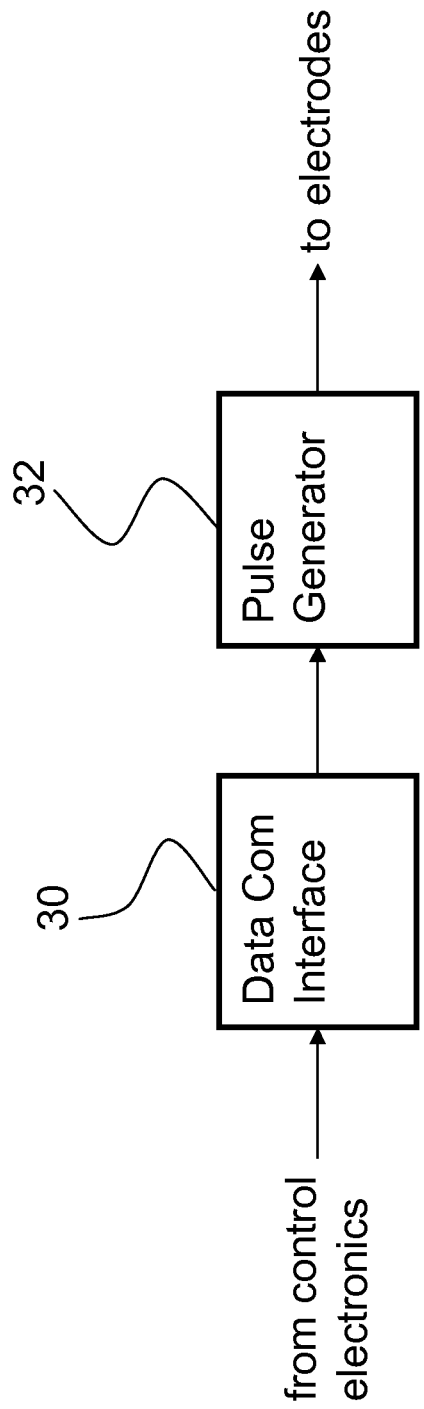
FIG. 3 is a schematic block diagram of a data communications interface and a communication pulse generator.
Figure 4:
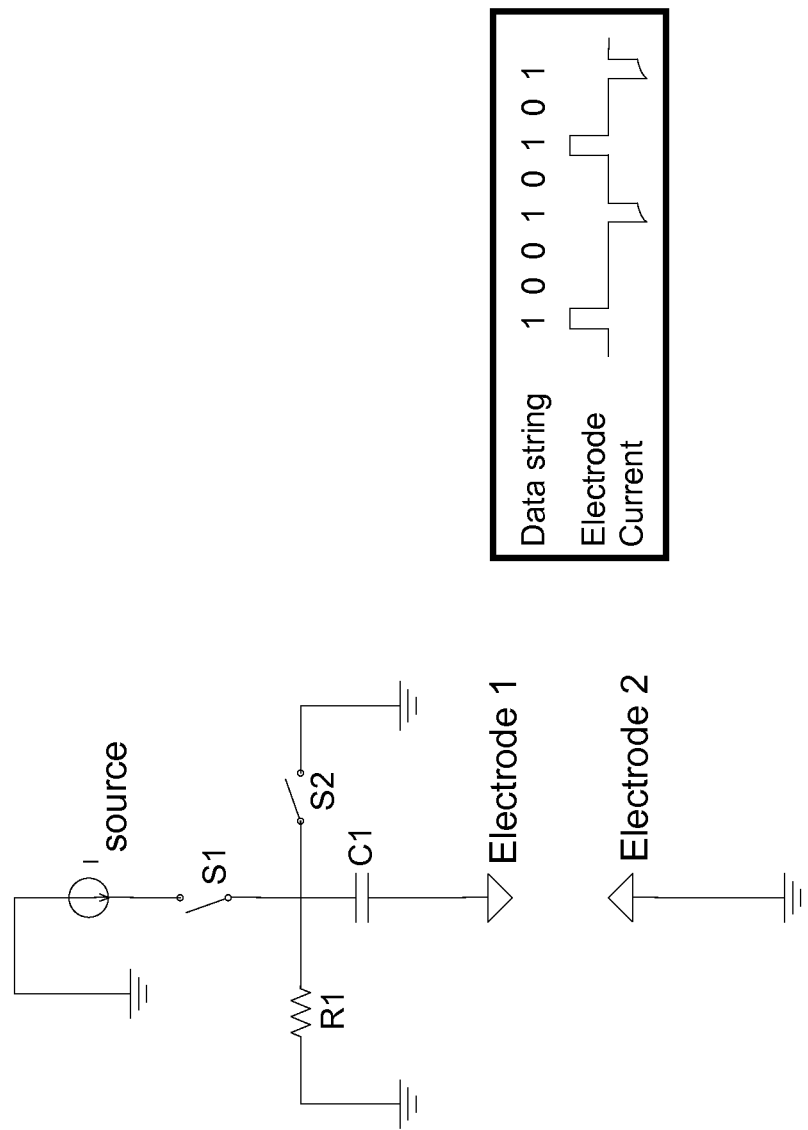
FIG. 4 illustrates details of the communication pulse generator and its pulse delivery circuitry.

FIG. 3 is a schematic block diagram of a data communications interface and a communication pulse generator. FIG. 4 illustrates details of the communication pulse generator and its pulse delivery circuitry. As shown in FIGS. 3 and 4, in at least one embodiment of the invention, the electronics module 24 may include one or more of a data communication interface 30 and a communication pulse generator 32 with pulse delivery circuitry.

As shown in FIG. 4, in at least one embodiment, the pulse delivery circuitry includes a current source $I_{source}$ connected to a capacitor C1 via a first switch S1. In one or more embodiments, the current source may be a constant current source. In at least one embodiment, the current source $I_{source}$ may be replaced by a voltage source connected to a capacitor C1 via the first switch S1. The voltage source, in one or more embodiments, provides a voltage and includes an internal resistance that limits the maximum current drawn. Thus, in at least one embodiment, the pulse delivery circuitry may generate and deliver electrical pulses that are either current pulses or voltage pulses. Capacitor C1, in one or more embodiments, may be connected to a first medical device surface electrode 1, such as electrode 16 or 18. At least one embodiment of the invention may include a second switch S2, that allows fast discharging the capacitor C1 via electrode 1, and may include an optional resistor R1 with relatively high ohmic resistance (e.g. 200 kΩ) that allows slow discharging of capacitor C1 in order to avoid unintended charge build-up.

According to one or more embodiments, in case of data communication when the pacemaker 10 is transmitting, a data string comprised of binary digits (bits; logical "1" and "0") may be put out by the pacemaker control electronics module 24 and received by the data communications interface 30.

In at least one embodiment, data communications interface 30 may perform a data whitening on a received data string in order to avoid long strings of logical "0"s in the data to be transmitted.

Generally, when an implanted medical device outputs current or voltage through electrodes, a charge balancing current is needed to ensure that the total charge through the electrode is neutral. Typically, this is utilized to minimize electrode corrosion, and it is required by standards such as EN 45502-2-1. In tone or more embodiments of the invention, the power required to transmit data may be minimized by utilizing both the forward current or voltage, and the charge balancing current or voltage as communication bits. As such, the power required to transmit data may be reduced by approximately half.

To use this technique, an implantable medical device according to at least one embodiment of the invention, for example pacemaker 10 sends a current or voltage pulse of alternating polarity for a logical "1" and no current or voltage for a logical "0". The first logical "1" bit, in at least one embodiment, is sent as a forward current or voltage pulse. In one or more embodiments, the forward current or voltage pulse may pass through a charge balancing capacitor on its way to the electrode. The forward current or voltage induces a charge on the charge balancing capacitor. In one or more embodiments, the communication pulse generator 32 or pulse delivery circuitry, respectively, of the implantable medical device 10 then holds this charge on the capacitor until the transmission time slot for the next logical "1" bit. During this time slot, in at least one embodiment, the pulse generator 32 or pulse delivery circuitry discharges the charge balancing capacitor through the electrodes. This induces a current or voltage through the electrodes of the opposite polarity of the initial forward current or voltage, and this reverse current or voltage comes at no additional energy cost (except for the relatively small current needed to drive the transmission logic). Thus, in the device and in the method, in at least one embodiment of the invention, both, forward current or voltage pulses and charge balancing (reverse) current or voltage pulses may be used to convey data. In one or more embodiments, this reduces by approximately on half, the transmit power requirements of the implantable medical device.

By way of at least one embodiment, to ensure that charge balancing is maintained through the electrodes, the implantable medical device 10 may include a moderately high impedance leakage path via resistor R1 to allow for any residual change on the charge balancing capacitor to bleed off though the electrodes. As such, charge balancing is maintained even if the communication windows end up with more charge flowing in one direction than the other.

In at least one embodiment, a data whitening algorithm may be used to ensure that long runs of logical "0"s are avoided, which might otherwise allow too much charge to bleed off the charge balancing capacitor in-between logical "1" bits.

By way of one or more embodiments, the current consumed by intra-body conductive telemetry may be cut by approximately half, and this in turn significantly reduces the size of the battery needed, and significantly reduces the size of the implantable medical device 10.

As shown in FIG. 4, operation of the pulse generator 32 and its pulse delivery circuitry is illustrated. In one or more embodiments, data whitening is used to avoid long strings of logical "1"s or "0"s in the data to be transmitted. When the first logical "1" is to be transmitted, in at least one embodiment, the switch S1 is closed, and the current $I_{source}$ flows through capacitor C1, and then through electrodes 1 and 2. At the end of the time slot for the first bit, in at least one embodiment, the S1 is opened and current stops flowing through the electrodes 1 and 2. At this point, capacitor C1 has been charged up by the current and is holding the charge. In one or more embodiments, the next time a logical "1" is to be transmitted, switch S2 is closed at the start of the bit window. As such, the capacitor C1 may discharge through the electrodes 1 and 2, resulting in current though the body of opposite polarity from the first logical "1" bit. In at least one embodiment, at the end of the time slot for this bit, switch S2 is opened and the current stops flowing through the electrodes. One or more embodiments of the invention may include the resistor R1, of large value (~200 kΩ), in order to ensure that, over time, no residual charge builds up on the capacitor, and when the data packet contains an odd number of logical "1"s, ensure that the charge from the last logical "1" has a path to dissipate through the electrodes. In at least one embodiment, switch S2 may be closed for an extended period of time (more than one bit window) at the end of each transmitted data packet. This ensures that any residual charge left of the capacitor C1 has time to discharge.

FIG. 5 illustrates intra-body communication between two implantable leadless pacemakers that together act as two chamber pacemaker. By way of one or more embodiments of the invention, the required battery current (to a first order) may be reduced in half, since the negative current pulse uses residual charge stored on the charge balancing capacitance rather than charge from the battery for power. In at least one embodiment, reducing the battery capacity needed to support conductive intra-body communications in half allows the use of very small implantable systems such as intracardiac leadless pacemaker 10. As shown in FIG. 5, one or more embodiments of the invention may include multi-chamber pacing systems with a plurality of implantable leadless pacemakers, such as pacemaker 10A (in the right atrium of a heart) and pacemaker 10V (in the right ventricle of a heart).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable medical device (10) configured to communicate via electric conductive body tissue comprising:
   a data communication interface (30), and
   a pulse generator (32),
      wherein the data communication interface (30) is connected to the pulse generator (32),
      wherein said pulse generator (32) is configured to generate and deliver forward electrical pulses and reverse electrical pulses, wherein a polarity of the reverse electrical pulses is opposite to the polarity of the forward electrical pulses,
      wherein said pulse generator (32) is configured to be controlled by said data communication interface (30),
      wherein said data communication interface (30) together with said pulse generator (32) are configured to
         generate electrical pulses representing binary digits, wherein a first kind of digits (1 or 0) is represented by an electrical pulse, and a second kind of digit respective of the other type of digits (0 or 1) is represented by a pause between electrical pulses, and,
         deliver electrical pulses with strictly alternating polarity, such that every other electrical pulse is a reverse electrical pulse of opposite polarity compared to an immediately preceding forward electrical pulse; and,
      wherein said pulse generator (32) is further configured to generate and deliver sub-threshold electrical pulses used to communicate data and supra threshold electrical pulses used to stimulate tissue.

2. The implantable medical device according to claim 1, wherein the first kind of binary digits represents a logical "1" and is represented by a electrical pulse and the second kind of binary digits represents a logical "0" and is represented by an absence of a electrical pulse.

3. The implantable medical device according to claim 1, wherein the first kind of binary digits represents a logical "0" and is represented by a electrical pulse and the second kind of binary digits represents a logical "1" and is represented by an absence of a electrical pulse.

4. The implantable medical device according to claim 1, wherein said data communication interface (30) together with said pulse generator (32) are further configured to provide a plurality of timeslots, wherein each timeslot of said plurality of time slots represents one binary digit.

5. The implantable medical device according to claim 1, wherein said data communication interface (30) is further configured to perform a whitening transformation on a data string prior to a transmission.

6. The implantable medical device according claim 1, wherein said pulse generator (32) comprises a pulse delivery circuitry comprising a capacitor (C1) configured to deliver a forward electrical pulse of said forward electrical pulses and a reverse electrical pulse of said reverse electrical pulses, such that the capacitor (C1) is charged upon delivery of said forward electrical pulse, and said capacitor (C1) is discharged when said reverse electrical pulse is delivered.

7. The implantable medical device according to claim 1, wherein said pulse generator (32) is further configured to deliver backward electrical pulses, wherein said forward electrical pulses and said backward electrical pulses comprise substantially a same amount of charge.

8. The implantable medical device according to claim 1, wherein said forward electrical pulse and said reverse electrical pulse are charge balancing and information encoding.

9. The implantable medical device according to claim 1, wherein each of said plurality of time slots comprises a same duration.

10. A method for data communication via electric conductive body tissue comprising:
   delivering electrical pulses representing binary digits,
   providing a plurality of time slots, wherein each time slot of said plurality of time slots represents one binary digit,
   delivering, in a respective time slot of said plurality of time slots, a forward or a reverse electrical pulse if a logical "1" is configured to be transmitted in said time slot or delivering no electrical pulse in case a logical "0" is to be transmitted in said time slot,
   alternating a polarity of said electrical pulses such that a next logical "1" is represented by a current or voltage of opposite polarity than a respective anteceding electrical pulse, and,
   generating and delivering sub-threshold electrical pulses to communicate data and supra threshold electrical pulses used to stimulate tissue.

11. The method for data communication via electric conductive body tissue according to claim 10, wherein said forward electrical pulse and said reverse electrical pulse are charge balancing and information encoding.

12. The method for data communication via electric conductive body tissue according to claim 10, wherein each of said plurality of time slots comprises a same duration.

13. A method for data communication to and from an implantable medical device via electric conductive body tissue comprising:
   generating and delivering forward electrical pulses and reverse electrical pulses, wherein a polarity of the reverse electrical pulses is opposite to the polarity of the forward electrical pulses from a pulse generator

(32) connected to and controlled by a data communication interface (30) of said implantable medical device;

generating electrical pulses representing binary digits, wherein a first kind of digits (1 or 0) is represented by an electrical pulse, and a second kind of digit respective of the other type of digits (0 or 1) is represented by a pause between electrical pulses via said data communication interface (30) and said pulse generator (32);

delivering electrical pulses with strictly alternating polarity, such that every other electrical pulse is a reverse electrical pulse of opposite polarity compared to an immediately preceding forward electrical pulse via said data communication interface (30) and said pulse generator (32); and, generating and delivering sub-threshold electrical pulses to communicate data and supra threshold electrical pulses used to stimulate tissue.

14. The method for data communication via electric conductive body tissue according to claim 13, further comprising providing one or more time slots, wherein each time slot of said one or more time slots represents one binary digit.

15. The method for data communication via electric conductive body tissue according to claim 10, further comprising performing a whitening transform on a data string prior to a transmission.

16. The method for data communication via electric conductive body tissue according to claim 10, further comprising delivering backward electrical pulses, wherein said forward electrical pulses and said backward electrical pulses comprise substantially a same amount of charge.

17. The method for data communication via electric conductive body tissue according to claim 10, wherein said forward electrical pulse is delivered via a capacitor such that the capacitor is charged upon delivery of said forward electrical pulse, and wherein said capacitor is discharged upon delivery of said reverse electrical pulse.

18. The method for data communication to and from an implantable medical device via electric conductive body tissue according to claim 14, wherein each of said plurality of time slots comprises a same duration.

* * * * *